United States Patent [19]

Vallarino

[11] Patent Number: 4,946,768

[45] Date of Patent: Aug. 7, 1990

[54] 3-AMINOALLYLIDENEMALONONITRILE UV-ABSORBING COMPOUNDS AND PHOTOGRAPHIC ELEMENTS CONTAINING THEM

[75] Inventor: Angelo Vallarino, Spontorno/Savona, Italy

[73] Assignee: Minnesota Mining and Manufacturing Company, St. Paul, Minn.

[21] Appl. No.: 881,066

[22] Filed: Jul. 2, 1986

[30] Foreign Application Priority Data

Jul. 11, 1985 [IT] Italy ............................... 21545 A/85

[51] Int. Cl.$^5$ .............................................. G03C 1/84
[52] U.S. Cl. .................................... 430/512; 430/507; 430/627; 430/628; 430/631; 430/931
[58] Field of Search .............. 430/507, 512, 931, 627, 430/628, 631

[56] References Cited

U.S. PATENT DOCUMENTS

| | | | |
|---|---|---|---|
| 4,045,229 | 3/1977 | Weber et al. ......................... | 430/512 |
| 4,195,999 | 4/1980 | Adachi et al. ....................... | 430/512 |
| 4,307,184 | 12/1981 | Beretta et al. ....................... | 430/512 |
| 4,443,534 | 4/1984 | Kojima et al. ....................... | 430/512 |
| 4,464,462 | 8/1984 | Sugimoto et al. .................... | 430/512 |
| 4,576,908 | 3/1986 | Vallarino et al. .................... | 430/512 |

*Primary Examiner*—Jack P. Brammer
*Attorney, Agent, or Firm*—Donald M. Sell; Walter N. Kirn; Mark A. Litman

[57] ABSTRACT

3-Aminoallylidenemalononitrile compounds corresponding to the formula:

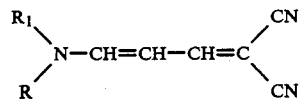

wherein $R_1$ is a short alkyl chain having 1 to 3 carbon atoms and R is a substituted or unsubstituted long alkyl chain greater than 10 carbon atoms, are useful in photography for absorbing ultraviolet radiations in the range from 360 to 400 nm, with no undesired absorption near 420 nm, when introduced in a photographic gelatin layer.

14 Claims, No Drawings

3-AMINOALLYLIDENEMALONONITRILE UV-ABSORBING COMPOUNDS AND PHOTOGRAPHIC ELEMENTS CONTAINING THEM

FIELD OF THE INVENTION

The present invention refers to UV-absorbing compounds and to photographic elements containing said compounds.

BACKGROUND OF THE ART

Silver halide emulsions are inherently sensitive to blue and ultraviolet radiation, while they are not sensitive to the green and red radiation. For normal color photographic processes, it is necessary to make these emulsions sensitive to green and red radiation by means of spectral sensitizers (e.g. cyanine dyes), well-known to the man skilled in the art.

It is also known that ultraviolet (UV) radiation may damage the color balance of the color photographic images (intended as the capacity of such images to reproduce real images with the same color balance as seen by human eye), because UV radiation causes an exposure, and therefore color formation, without any correspondence to the real image, as seen by human eyes, which do not see UV radiation, i.e. those shorter than about 420 nm.

Such radiation, furthermore, has destroying effects on the elements which form the photographic image when they are exposed to the light after having been processed (for instance color paper, after exposure and processing, undergoes a color degradation if it does not contain a suitable ultraviolet absorber).

Some compounds, such as hydroxy-phenylbenzotriazole compounds, capable of protecting photographic materials from destroying effects of UV radiations, have been described in U.S. Pat. Nos. 3,004,896; 3,253,921; 4,323,633. Such compounds have found large use in photography, particularly in color photography.

These compounds cannot be used, however, to prevent UV radiation from disturbing the chromatic equilibrium of photographic images.

To accomplish this result, compounds must absorb the ultraviolet radiation near 400 nm and not that near 420 nm, while the above mentioned hydroxy-phenyl-benzotriazole compounds absorb between 300 and 370 nm.

Even if some compounds with such absorption characteristics were known, they can loose those characteristics when introduced into the photographic layers by the normal techniques known in the art, such as the dispersion technique. An example of this is represented by the 3-dialkylaminoallylidenemalononitrile compounds described in U.S. Pat. No. 30,303 wherein the two alkyl chains, being the same or different, each contain 1 to 10 carbon atoms, which have shown to be compounds with a high and sharp absorption near 400 nm (and a high molar extinction coefficient), without absorbing the radiations near 420 nm. Unfortunately, they have been shown to loose their characteristics when introduced in the photographic layer according to the above mentioned dispersion method. In fact, when the alkyl chains are short (1 to 3 carbon atoms), they tend to crystallize or to diffuse into the layers; when the alkyl chains are long (at least 4 carbon atoms) they exhibit an undesired absorption at 415 nm. To obviate this disadvantage, the loaded polymer technique has been suggested (see BE patent 833,512) which consists of loading solid particles of a particular polymeric latex with an aminoallylidenemalononitrile hydrophobic derivative and mixing the so loaded latex with the gelatin of the photographic layer, in which the UV absorber compound must be introduced. This technique, however, has the disadvantage that it is not suitable for obtaining consistent, reproducible results. Besides, not every polymeric latex is suitable with this process and those that are suitable are difficult to prepare and expensive to purchase. Furthermore, the high latex/UV absorber compound ratio makes necessary the use of quantities of latex which are too high and negatively affect the physical characteristics of the layer containing it.

Polymeric compounds including ultraviolet absorbing aminoallylidene units, obtained upon copolymerization of 3-aminoallylidenemalononitrile with an ethylenically unsaturated monomer (such as an acrylic monomer), have been described in U.S. Pat. No. 4,307,184, but this technique seems more complicated than the normal dispersion techniques known in the art (see for example U.S. Pat. Nos. 2,322,027; 2,533,514; 2,801,171; 2,870,012; 2,991,177; 2,739,888; 3,253,921 and in British patent 1,357,372).

Such solvent dispersion technique consists of dissolving a compound in an organic solvent and then dispersing the obtained solution with an aqueous medium, such as water or a gelatin in water solution. The obtained dispersion can either be directly introduced into the photographic composition before coating or can be dried to remove part or all organic solvent prior to such introduction. In one case, high-boiling (water immiscible) organic solvents are to be used. In the other case, low-boiling organic solvents are to be used alone or mixed with high-boiling organic solvents.

SUMMARY OF THE INVENTION

The present invention refers to 3-aminoallylidenemalononitrile compounds, useful in photography to absorb ultraviolet radiations, corresponding to the general formula:

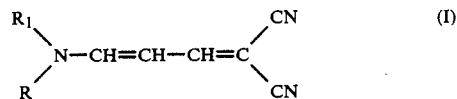

wherein $R_1$ is a short alkyl chain having 1 to 3 carbon atoms and R is a substituted or unsubstituted long alkyl chain greater than 10 carbon atoms.

The present invention refers also to a photographic material in one of its layers including a compound corresponding to general formula (I).

The compounds of this invention show a good absorption in the range from 360 to 400 nm and show no undesired absorption near 420 nm (or no significant absorption near 415 nm). They can be introduced into the photographic layers by the above indicated dispersion technique to obtain the desired results (but can also be introduced into photographic layers in an alkaline water solution or in any other kind of methods known in the art) without losing their absorption and non-diffusing characteristics.

DETAILED DESCRIPTION OF THE INVENTION

According to the present invention it has been found that the combination of a short alkyl chain, preferably an unsubstituted alkyl group having 1 to 3 carbon atoms, with a long alkyl chain (substituted or not substituted), preferably having at least 10 carbon atoms as substituents of the amino group of a 3-aminoallylidenemalononitrile compound provides compounds having the desired behaviour as regards both their UV absorption (absorption in the range from 360 to 400 nm with no undesired absorption near 420 nm) and non-diffusing properties.

Accordingly, the present invention relates to 3aminoallylidenemalononitrile compounds useful in photography to absorb ultraviolet radiations, corresponding to the general formula:

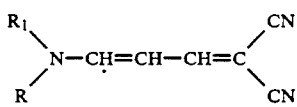

wherein $R_1$ is a short alkyl chain having 1 to 3 carbon atoms, preferably a methyl or ethyl group, and R is a substituted or unsubstituted alkyl chain greater than 10 carbon atoms. In particular, in the above formula, R is an alkyl chain of formula $R_2(A)_n R'_2$, wherein $R_2$ is hydrogen or an alkyl group, $R'_2$ is an alkylene group, A is a divalent radical (the expression "divalent radical" is used herein to indicate any divalent residue which is included in a photographically useful organic molecule to link an alkyl group to a functional compound (in this case an aminoallylidenemalononitrile UV absorbing compound, in other similar cases a coupler compound) or a divalent residue such as -O-, -COO-, -SO₃-, which together with hydrogen respectively form a hydroxy, carboxy or sulfoxy group) and n is 0 or 1, the total sum of carbon atoms in $R_2$ and $R'_2$ being greater than 10 and, preferably, equal or less than 23.

When n is 0, $R_2$ and $R'_2$ form an alkyl chain greater than 10 carbon atoms, such as a decyl, a dodecyl, a tetradecyl, a hexadecyl, a pentadecyl, an octadecyl group. Preferred examples of the divalent radical A are oxygen, carbonyl, sulfonyl, sulfoxy, carboxy, carbonamido and sulfonamido. In case of A being a sulfoxy or carboxy or oxygen, $R_2$ may be equal to hydrogen when R is required to provide a hydrophilic terminal group of the -COOH, -SO₃H or -OH type in order to make the compound soluble in water or aqueous alkaline solutions. Of course, such hydrophilic group may be attached to the alkyl chain in a non-terminal position. The alkyl chain can be substituted with one or more substituents such as alkyl groups, halogen atoms, nitro groups and cyano groups. Examples of R in the above formula are the following: $C_{10}H_{21}$-, $C_{12}H_{25}$-, $C_{14}H_{29}$-, $C_{15}H_{31}$-, $C_{16}H_{33}$-, $C_{18}H_{37}$-, $C_{20}H_{41}$-, $C_{12}H_{25}$-NH-CO-CH₂-, $C_{12}H_{25}$-CO-CH₂-, $C_{10}H_{21}$-O-CO-CH₂-, $C_{10}H_{21}$-NH-SO₂-CH₂-, $C_{12}H_{25}$-O-C₂H₄-CO-CH₂-$C_{10}H_{21}$-SO-CH₂-, $C_{10}H_{21}$-SO₂-CH₂-, HSO₃-(CH₂)₁₂-CH₂-HCO₂-(CH₂)₁₄-CH₂-, $C_{12}H_{25}$-CO-NH-CH₂-CO-CH₂-, OH-CH₂-CO-(CH₂)₁₀-CH₂-, $C_{10}H_{21}$-CO-CHCH-CO-CH₂-, $C_{10}F_{21}$-CO-CH₂-,

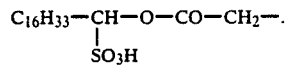

According to another aspect, the present invention relates to a photographic material comprising at least one silver halide emulsion layer and at least an auxiliary layer coated on a supporting base, one of said layers including, dispersed therein, a 3-aminoallylidenemalononitrile compound of formula (I), wherein $R_1$ is a short alkyl chain of 1 to 3 carbon atoms, preferably a methyl or ethyl group and R is a substituted or unsubstituted long alkyl chain greater than 10 carbon atoms In particular, in the above formula, R is an alkyl of formula $R_2(A)_n R'_2$, wherein $R_2$, $R'_2$, A and n have the hereinbefore mentioned meanings. Preferably, the present invention relates to the above mentioned photographic material, in which said layer is an auxiliary layer, in particular an external protective layer. More preferably, such layers are substantially made of gelatin.

In particular, the present invention refers to the above mentioned photographic material, in which said silver halide emulsion layer is optically sensitized and is associated with a color forming coupler.

More in particular, the present invention refers to the above photographic material in which said silver halide emulsion layer or auxiliary layer contains, dispersed therein, a 3-aminoallylidenemalononitrile compound of formula (I) dissolved in fine droplets of high-boiling waterimmiscible or substantially water-immiscible organic solvent.

There are some different ways to introduce into the photographic layers the compounds of the present invention. They present useful photographic properties dealing with the absorption as indicated above when they are directly or indirectly dispersed into the photographic layers ("directly dispersed" meaning dispersed after having been dissolved in water or in organic solvents in the art and "indirectly dispersed" meaning dispersed through a physical or chemical association different from a solution, such as the chemical-physical association established between the compound and a polymeric latex according to the loaded latex technique or in the chemical association established in a polymer among different monomer units).

As already indicated, it is preferable to introduce such compound into the photographic layers by the dispersion technique. Such techniques are very useful for introducing different products in the same dispersion, for example couplers and other auxiliaries such as UV absorbers.

In the present invention, it has been found to be useful, for example, to use a combination of a 3-aminoallylidenemalononitrile compound of formula (I) with a (hydrophobic) 2-(2'-hydroxy-phenyl)-benzotriazole compound dispersed in a photographic layer dissolved (together) in the same high-boiling water-immiscible organic solvent.

Particularly useful solvents for this technique are those described in the above cited patents. High-boiling organic solvents within the group of phosphate esters are, in particular, triphenylphosphate, tricresylphosphate, diphenyl-mono-p-tert.-butylphenylphosphate, monophenyldi-p-tert -butylphenylphosphate, diphenyl-mono-o-chlorophenylphosphate, monophenyl-di-o-chlorophenylphosphate, tri-p-tert.-butylphenylphosphate, tri-o-phenylphosphate, di-p-tert.-butylphenyl-mono-(5-tert.-butyl-2-phenyl)-phosphate.

High-boiling organic solvents within the group of amides are the following: acetyl-n-butylaniline, acetyl-methyl-p-toluidine, benzoylpiperidine, N-n-amylphthalimide, N-n-amylsuccinimide; N-2-cyanobutyl-phthalimide, N,N-di-ethyllauramide, N,N-di-n-butyl-lauramide, N,N-diethylester-amide, N,N-diethylcapa-mide, N,N-dipropylacetamide, N,N-ethylbutyllaura-mide, N,N-didecyllauramide, N,N-dinonylester-amide, N,N-dibutylarachidamide, N,N-dibutylcaproamide, N,N'-tetrabutyl-succinamide, N,N'-tetrahexyladipa-mide, N,N'-tetradecylmalonamide.

High-boiling solvents can be chosen also within the group of phthalates, such as methylphthalate, ethylphthalate, propylphthalate, n-butylphthalate, di-n-butylphthalate, n-amylphthalate, isoamylphthalate and dioctylphthalate.

Low-boiling water-insoluble organic solvents include methyl, ethyl, propyl and butyl acetates, isopropylace-tate, ethylpropionate, sec.-butylalcohol, carbontetra-chloride and chloroform. Water-soluble organic solvents (which are removed from the emulsions by washing with water) include methyl isobutylketone, β-ethox-yethylacetate, β-butoxy-β-ethoxyethylacetate (die-thyleneglycolmonoacetate), methoxy-triglycolacetate, methylcellosolve acetate, acetonylacetone, diacetone alcohol, butylcarbitol, ethyleneglycolmonobutylether, methylcarbitol, ethyleneglycolmonomethylether, ethyl-eneglycol, diethyleneglycol and dipropyleneglycol.

The compounds of the present invention have also good absorption characteristics when loaded onto a latex according to the loaded latex technique known in the art (see for example U.S. Pat. Nos. 4,133,687; 4,199,363; 4,214,047) but the result is considered of less importance with respect to the fact that the same compound can be used with the dispersion technique to obtain the desired results.

The compounds of the present invention can be also introduced into the photographic layers in water or in alkaline water solution; in such a case they need to contain at least a OH group or an acid solubilizing group of the SO$_3$H or COOH type. In this case, the above indicated R alkyl chain must be a substituted one and it needs to have among the substituents such kind of groups cited above in order to favor the solubility of the compound of formula (I) of the present invention in water or in an alkaline water solution.

EXAMPLE 1

3-N-methyl-N-dodecylaminoallylidenemalononitrile

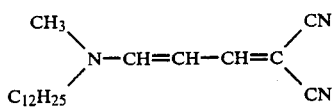

A solution of 237 g (1 M) of acetoanilidoal-lylidenemalononitrile (prepared as described in RE 30,303) in 300 ml of ethanol was added with 285.3 g (1.07 M of product 75%) of n-methyl-n-dodecylamine. The mixture was refluxed for 1 hour, then the red solution, thus obtained, was concentrated under vacuum and cooled at -4° C. The separated yellowish crystals were filtered and dried at room temperature. The obtained product (189.3 g, yield 63%) had a melting point of 48-50° C.; γmax (methanol) =377 nm; ε methanol =55400.

Percent analysis for C$_{19}$H$_{31}$N$_3$:

|  | Found | Calculated |
|---|---|---|
| N % | 13.92 | 13.95 |
| C % | 75.71 | 75.77 |
| h % | 10.47 | 10.37 |

EXAMPLE 2

3-N-ethyl-N-dodecylaminoallylidenemalononitrile (Compound 2)

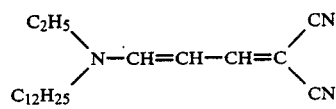

This compound was prepared in the same manner as described in Example 1, starting from N-ethyl-N-dodecylamine and acetoanilidoallylidenemalononitrile in ethanol solution. The compound was purified by fractionation through a silica gel column using 60/40 benzene/ethylacetate as eluent. The yield of the obtained red-yellow oil was 72.4%. The product had a γmax (methanol) =377 nm; ε=54500.

Percent analysis for C$_{20}$H$_{33}$N$_3$:

|  | Found | Calculated |
|---|---|---|
| H % | 13.37 | 13.33 |
| C % | 76.38 | 76.20 |
| N % | 10.52 | 10.47 |

EXAMPLE 3

3-N-hexadecylaminoallylidenemalononitrile (Compound 3)

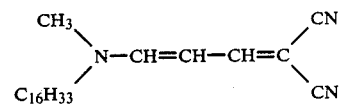

Such compounds was prepared starting from the N-methyl-N-hexadecylamine and the acetoanilidoal-lylidenemalononitrile in refluxing ethanol. Yield: 83%. M.P.: 68°-70° C. γmax (methanol)=377. ε methanol=58000.

Percent analysis for C$_{23}$H$_{39}$N$_3$:

|  | Found | Calculated |
|---|---|---|
| H % | 13.92 | 13.95 |
| C % | 75.71 | 75.77 |
| N % | 10.47 | 10.37 |

EXAMPLE 4

3-N-methyl-N-octadecylaminoallylidenemalononitrile (Compound 4)

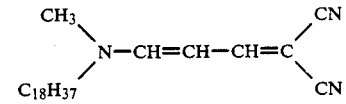

This compound was prepared as described in Example 1, starting from N-methyl-N-octadecylamine and acetoanilidoallylidenemalononitrile. The product was crystallized from ethanol. Yield=60%. M.P.=73-75° C. γmax (methanol)=377 nm. ε=47000.

Percent analysis for $C_{25}H_{43}N_3$:

|   | Found | Calculated |
|---|---|---|
| N % | 9.26 | 9.32 |
| C % | 76.10 | 76.36 |
| H % | 11.21 | 11.24 |

EXAMPLE 5
N-3-allylidenemalononitrile-decylsarcosinate
(Compound 5)

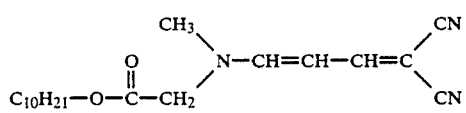

10 g (0.26 M) of 3-aminoallylidenemalononitrile sarcosine were added to 41.45 g (0.052 M) of decadecyl alcohol, then 0.3 g of p-toluensulfonic acid and 3 drops of sulfonic acid were added. The mixture was refluxed for 18-20 hours at the temperature of 80° C. Then 170 ml of methyl alcohol were added. After about 5 minutes the mixture was filtered and cooled. Yellowish crystals separated: 9.16 g; yield 54%; M.P. 81-84° C.; εmax (methanol) 374ε=58834.

Percent analysis for $C_{19}H_{29}N_3O_2$:

|   | Found | Calculated |
|---|---|---|
| N % | 12.58 | 12.68 |
| C % | 68.59 | 68.85 |
| H % | 8.90 | 8.82 |

EXAMPLE 6

Five compositions, each containing a UV absorbing compound of the present invention, were prepared according to the following formulation:

| UV absorbing compound | 8 g |
|---|---|
| Tricresylphosphate | 1.5 g |
| Dibutylphthalate | 1.5 g |
| Ethylacetate | 10 ml |
| 10% Aqueous gelatin | 24 ml |
| 5% Aqueous sodium alkylnaphthalene sulfonate | 10 ml |

Each composition was stirred with a Laboratory Mixer Emulsifier of Silverson Machines Ltd. at 40° C. for 5 minutes. Five dispersions were obtained each comprising a UV absorbing compound of the present invention dissolved in fine droplets of a water-immiscible solvent dispersed in gelatin.

Each dispersion was then incorporated into the intermediate layer in a negative photographic material comprising a support base, one or more red-sensitive silver halide emulsion layers, having incorporated therein cyanforming couplers dispersed in the layers in oil particles, one or more green-sensitive silver halide emulsion layers, having incorporated therein magenta-forming couplers dispersed in the layers in oil particles, one or more bluesensitive silver halide emulsion layers, having incorporated therein yellow-forming couplers dispersed in the layers in oil particles, the above mentioned intermediate layer and an external top coating layer. The gelatin interlayer contained the compound of the present invention in a quantity as to give 0.124 g/m², 1.47 g/m² of gelatin. The top coat layer contained a matting agent, such as polymethylmethacrylate, as to give 0.283 g/m² of gelatin.

Five films (Films 1 to 5), respectively containing the UV absorbing compounds 1 to 5 of the present invention were obtained. In a similar way a comparison film (Film 6) was prepared comprising in the intermediate layer the 3dihexylaminoallylidenemalononitrile UV absorbing compound (Compound B of Reissued patent 30,303), dispersed with the same procedure described above, at the coverage of 0.124 g/m². A second comparison film (Film 7) was then prepared without UV absorbing compound in the intermediate layer.

Samples of such films were exposed through a Jarrel Ash Spectrograph, then subjected to a C-41 processing and spectra at fog levels of the processed films were read at a Perkin Elmer Spectrophotometer. Other samples of such films were further exposed through a 0.30 continuous wedge densitometer, then processed as said hereinabove to evaluate the relative speed of yellow layers.

The following table reports the optical density values read at the spectrophotometer at 382 nm and at 415 nm and the yellow relative speeds of the films containing compounds 1 to 5 of the present invention compared with the film containing the 3-dihexylaminoallylidenemalononitrile compound (Compound B) described in RE 30,303 and the film which did not contain any kind of UV absorbing compound.

| Films | UV-absorb. compound | O.D. 382 nm | O.D. 415 nm | logE 0.20 O.D. above fog | logE 1.0 O.D. above fog |
|---|---|---|---|---|---|
| 1 | Comp. 1 | 0.63 | 0.02 | 19.5 | 6.8 |
| 2 | Comp. 2 | 0.67 | 0.02 | 19.4 | 6.5 |
| 3 | Comp. 3 | 0.58 | 0.02 | 19.5 | 6.2 |
| 4 | Comp. 4 | 0.61 | 0.02 | 19.3 | 5.9 |
| 5 | Comp. 5 | 0.59 | 0.02 | 19.4 | 5.9 |
| 6 | Comp. B | 0.60* | 0.46 | 18.5 | 5.0 |
| 7 | — | — | — | 21.0 | 8.5 |

*The optical density value of Compound B was read at a spectrophotometer at 375 nm, instead of 382 nm, where the compound has the maximum optical density.

The above reported data show that, using Compounds 1 to 5 of the present invention rather than Compound B described in RE 30,303, a lower loss of speed is obtained with respect to a film not containing any UV absorbing compound.

I claim:

1. A photographic material comprising a support base, at least one silver halide gelatin emulsion layer and at least one auxiliary layer over said silver halide emulsion layer, said photographic material being characterized by having at least one of said emulsion and auxiliary layers containing a radiation absorbing amount of a compound of the formula:

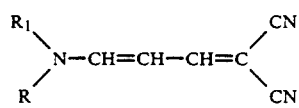

wherein $R_1$ is a short alkyl chain having 1 to 3 carbon atoms and R is a substituted or unsubstituted long alkyl chain greater than 10 carbon atoms and up to 20 carbon atoms.

2. The photographic material of claim 1, in which said compound is in an auxiliary layer which is an external protective layer.

3. The photographic material of claim 1, wherein said emulsion layer and said auxiliary layer are made of gelatin.

4. The photographic material of claim 1, wherein said silver halide emulsion layer has photographic couplers dispersed therein.

5. The photographic material of claim 1, wherein said compound is dissolved in fine droplets of a high-boiling water-immiscible organic solvent.

6. The photographic material of claim 5, wherein said compound is dispersed in combination with a hydroxyphenylbenzotriazole compound dissolved in fine droplets of the same high-boiling water-immiscible organic solvent.

7. A photographic material comprising a support base, at least one silver halide gelatin emulsion layer and at least one auxiliary layer over said silver halide emulsion layer, said photographic material being characterized by having at least one of said layers containing an ultraviolet radiation amount of 0.124 to 1.47 g/m² of gelatin of a compound of the formula:

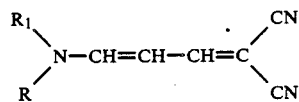

wherein $R_1$ is a short alkyl chain having 1 to 3 carbon atoms and R is a substituted or unsubstituted long alkyl chain with greater than 10 carbon atoms and up to 20 carbon atoms.

8. The photographic material of claim 7, in which said compound is in an auxiliary layer which is an external protective layer.

9. The photographic material of claim 7, wherein said emulsion layer and said auxiliary layer are made of gelatin.

10. The photographic material of claim 7, wherein said silver halide emulsion layer has photographic couplers dispersed therein.

11. The photographic material of claim 1 wherein said long alkyl chain is unsubstituted.

12. The photographic material of claim 7 wherein said long alkyl chain is unsubstituted.

13. The photographic material of claim 1 wherein said long alkyl chain has a substituent selected from the group consisting of alkyl groups, halogen atoms, nitro groups, and cyano groups.

14. The photographic material of claim 7 wherein said long alkyl chain has a substituent selected from the group consisting of alkyl groups, halogen atoms, nitro groups, and cyano groups.

* * * * *

UNITED STATES PATENT AND TRADEMARK OFFICE
CERTIFICATE OF CORRECTION

PATENT NO. : 4,946,768
DATED : August 7, 1990
INVENTOR(S) : Vallarino

It is certified that error appears in the above-identified patent and that said Letters Patent is hereby corrected as shown below:

Column 3, line 64, "$C_{12}H_{25}-O-C_2H_4-CO-CH_2-C_{10}H_{21}-SO-CH_2-$,"
should be -- $C_{12}H_{25}-O-C_2H_4-CO-CH_2-$, $C_{10}H_{21}-SO-CH_2-$ --.

Column 3, line 65, "$HSO_3-(CH_2)_{12}-CH_2-HCO_2-(CH_{214}CH_2-$,"
should be -- $HSO_3-(CH_2)_{12}-CH_2-$, $HCO_2-(CH_2)_{14}-CH_2-$, --.

Column 3, line 67, "$C_{10}H_{21}-CO-CHCH-CO-CH_2-$," should be
-- $C_{10}H_{21}-CO-CH=CH-CO-CH_2-$ --.

Column 5, line 53, insert --(Compound 1)-- after "3-N-methyl-N-dodecylaminoallylidenemalononitrile".

Column 6, line 48, insert --The crude product was recrystallized in 96% ethanol.-- after "ethanol."

Signed and Sealed this

Fifth Day of November, 1991

Attest:

HARRY F. MANBECK, JR.

Attesting Officer

Commissioner of Patents and Trademarks